United States Patent [19]

Pitteloud

[11] Patent Number: 5,449,777
[45] Date of Patent: Sep. 12, 1995

[54] PHENOLIC S-TRIAZINES

[75] Inventor: Rita Pitteloud, Praroman, Switzerland

[73] Assignee: Ciba-Geigy Corporation, Ardsley, N.Y.

[21] Appl. No.: 270,066

[22] Filed: Jul. 1, 1994

[30] Foreign Application Priority Data

Jul. 8, 1993 [CH] Switzerland .................. 2050/93

[51] Int. Cl.⁶ .................. C07D 251/30; C07D 251/38; C07D 251/40; C07D 403/04
[52] U.S. Cl. .................. 544/208; 544/113; 544/194; 544/209; 544/211; 544/213; 544/219; 544/83
[58] Field of Search .............. 544/113, 209, 219, 194, 544/208, 211, 212, 213

[56] References Cited

U.S. PATENT DOCUMENTS

| | | | |
|---|---|---|---|
| 3,925,376 | 12/1975 | Chalmers et al. | 544/198 |
| 4,042,562 | 8/1977 | Hofer et al. | 544/198 |
| 4,086,204 | 4/1978 | Cassandrini et al. | 544/207 |
| 4,108,829 | 8/1978 | Cassandrini et al. | 544/209 |
| 4,161,592 | 7/1979 | Evans et al. | 251/46 |
| 4,234,707 | 11/1980 | Rody et al. | 525/437 |
| 4,268,593 | 5/1981 | Leppard et al. | 430/17 |
| 4,294,963 | 10/1981 | Rody | 544/198 |
| 4,452,884 | 6/1984 | Leppard | 430/551 |
| 4,584,265 | 4/1986 | Leppard et al. | 430/551 |
| 4,972,014 | 11/1990 | Hayes et al. | 524/219 |
| 5,086,096 | 2/1992 | Kosinski | 524/36 |
| 5,106,888 | 4/1992 | Kosinski | 524/35 |

Primary Examiner—Yogendra N. Gupta
Attorney, Agent, or Firm—Luther A. R. Hall; Michele A. Kovaleski

[57] ABSTRACT

Compounds of formula I

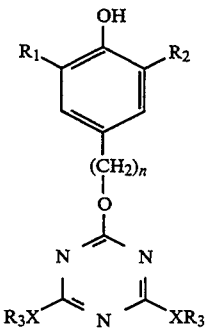

wherein
$R_1$ and $R_2$ are each independently of the other hydrogen, $C_1$–$C_{24}$alkyl, phenyl-substituted $C_1$–$C_4$alkyl, unsubstituted or $C_1$–$C_4$alkyl-substituted $C_5$–$C_8$cycloalkyl, unsubstituted or $C_1$–$C_4$alkyl-substituted phenyl, with the proviso that both substituents $R_1$ and $R_2$ are not simultaneously hydrogen,
n is an integer from 3 to 8,
$R_3$ is $C_1$–$C_{18}$alkyl, $C_2$–$C_8$alkyl which is interrupted by —O—, —S— or —$NR_4$—, unsubstituted or $C_1$–$C_4$alkyl-substituted $C_5$–$C_8$cycloalkyl, phenyl-substituted $C_1$–$C_4$alkyl, unsubstituted or $C_1$–$C_{12}$alkyl-substituted phenyl or a radical —($CH_2$)$_m$—$COOR_4$ or

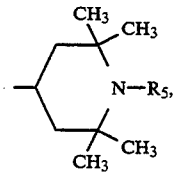

$R_4$ is $C_1$–$C_{18}$alkyl, unsubstituted or $C_1$–$C_4$alkyl-substituted $C_5$–$C_8$cycloalkyl, benzyl or phenyl,
$R_5$ is hydrogen, methyl, benzyl or a radical —$OR_7$,
m is 1 or 2,
X is O, S, or $NR_6$, and
$R_6$ is hydrogen or $C_1$–$C_{12}$alkyl, or
$R_3$ and $R_6$ together with the linking N-atom are a radical

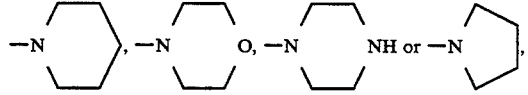

and
$R_7$ is $C_1$–$C_{12}$alkyl
are suitable stabilisers for organic materials.

8 Claims, No Drawings

PHENOLIC S-TRIAZINES

The present invention relates to novel phenolic s-triazines, to the use thereof as stabilisers for organic materials susceptible to thermal, oxidative and/or light-induced degradation, and to compositions comprising said novel compounds.

A color photographic recording material that contains s-triazines as stabilisers is disclosed in U.S. Pat. No. 4,584,265. 1,3,5-Triazines containing at last one sterically hindered amino and phenol group are disclosed as light stabilisers and antioxidants for polymeric materials in U.S. Pat. No. 4,161,592.

There is still a need to provide effective stabilisers for organic materials susceptible to thermal, oxidative and/or light-induced degradation.

Surprisingly, it has now been found that specific phenolic s-triazines have excellent stabilising properties for these substrates.

Accordingly, the invention relates to compounds of formula I

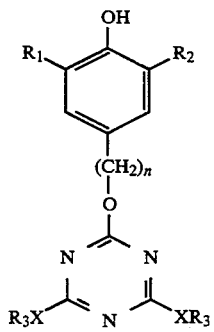

wherein
R$_1$ and R$_2$ are each independently of the other hydrogen C$_1$-C$_{24}$alkyl, phenyl-substituted C$_1$-C$_4$alkyl, unsubstituted or C$_1$-C$_4$alkyl-substituted C$_5$-C$_8$cycloalkyl, unsubstituted or C$_1$-C$_4$alkyl-substituted phenyl, with the proviso that both substituents R$_1$ and R$_2$ are not simultaneously hydrogen,
n is an integer from 3 to 8,
R$_3$ is C$_1$-C$_{18}$alkyl, C$_2$-C$_8$alkyl which is interrupted by —O—, —S— or —NR$_4$—, unsubstituted or C$_1$-C$_4$alkyl-substituted C$_5$-C$_8$cycloalkyl, phenyl-substituted C$_1$-C$_4$alkyl, unsubstituted or C$_1$-C$_{12}$alkyl-substituted phenyl or a radical —(CH$_2$)$_m$—COOR$_4$ or

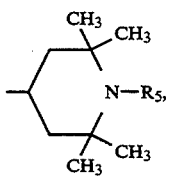

R$_4$ is C$_1$-C$_{18}$alkyl, unsubstituted or C$_1$-C$_4$alkyl-substituted C$_5$-C$_8$cycloalkyl, benzyl or phenyl,
R$_5$ is hydrogen, methyl, benzyl or a radical —OR$_7$,
m is 1 or 2,
X is O, S, or NR$_6$, and
R$_6$ is hydrogen or C$_1$-C$_{12}$alkyl, or
R$_3$ and R$_6$ together with the linking N-atom are a radical

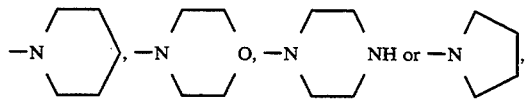

and
R$_7$ is C$_1$-C$_{12}$alkyl.

R$_1$, R$_2$, R$_3$ and R$_4$ defined as C$_1$-C$_{18}$alkyl may be linear or branched and are typically methyl, ethyl, n-propyl, isopropyl, n-butyl, s-butyl, tert-butyl, isobutyl, pentyl, hexyl, octyl, nonyl, decyl, dodecyl, or octadecyl. R$_1$ and R$_2$ as C$_1$-C$_{24}$alkyl may additionally be linear or branched eicosyl, heneicosyl, docosyl or tetracosyl. R$_1$ and R$_2$ are preferably C$_1$-C$_8$alkyl, typically C$_1$-C$_4$alkyl, preferably methyl or tert-butyl. R$_4$ is preferably a mixture of octyl isomers.

R$_6$ and R$_7$ defined as C$_1$-C$_{12}$alkyl are linear or branched and are typically methyl, ethyl, n-propyl, isopropyl, n-butyl, sec-butyl, tert-butyl, isobutyl, pentyl, hexyl, 2-ethylhexyl, octyl, nonyl, decyl or dodecyl. R$_6$ is for example C$_1$-C$_8$alkyl, specifically C$_1$-C$_4$alkyl, preferably methyl.

R$_3$ defined as C$_2$-C$_8$alkyl interrupted by —O—, —S— or —NR$_4$— is typically a group —(CH$_2$)$_x$OCH$_3$, —(CH$_2$)$_x$OC$_2$H$_5$, —(CH$_2$O)$_x$CH$_3$, —(CH$_2$O)$_x$C$_2$H$_5$, —(CH$_2$CH$_2$O)$_x$CH$_3$, —(CH$_2$CH$_2$O)$_x$C$_2$H$_5$, —(CH$_2$)$_x$SCH$_3$, —(CH$_2$)$_x$SC$_2$H$_5$, wherein x is 1–20.

R$_1$, R$_2$, R$_3$ and R$_4$ defined as C$_5$-C$_8$cycloalkyl are cyclopentyl, cyclohexyl, cycloheptyl and cyclooctyl, preferably cyclopentyl and cyclohexyl. If these radicals are substituted by C$_1$-C$_4$alkyl, then they may carry 1 to 3, preferably 1 to 2, alkyl substituents and, most preferably, 1 alkyl substituent. Typical examples of such substituted radicals are methylcyclopentyl, methylcyclohexyl, dimethylcyclopentyl and ethylcyclopentyl.

R$_1$, R$_2$ and R$_3$ defined as phenyl-substituted C$_1$-C$_4$alkyl are typically benzyl, α,α-dimethylbenzyl, α-methylbenzyl, 1-phenylethyl, 2-phenylethyl or phenylbutyl. Benzyl is preferred.

The phenyl ring in phenyl-substituted C$_1$-C$_4$alkyl groups R$_1$, R$_2$ and R$_3$ may contain 1 to 3, preferably 1 to 2, alkyl substituents and, most preferably, 1 alkyl substituent. Typical examples are tolyl, xylyl, mesityl, ethylphenyl, diethylphenyl, propylphenyl, isopropylphenyl or butylphenyl. The phenyl ring in R$_3$ may be substituted by C$_1$-C$_{12}$alkyl and is typically octylphenyl, nonylphenyl or dodecylphenyl.

R$_3$ is preferably C$_1$-C$_{12}$alkyl, typically C$_1$-C$_8$alkyl and —(CH$_2$)$_m$—COOR$_4$.

R$_5$ is preferably hydrogen or methyl, most preferably methyl.

R$_6$ is preferably hydrogen or methyl.

Compounds of formula I, wherein X is S or NR$_6$, preferably S, are preferred.

Further interesting compounds of formula I are those wherein n is an integer from 4 to 6.

To be singled out for special mention are compounds of formula I, wherein R$_1$ and R$_2$ are each independently of the other C$_1$-C$_4$alkyl or cyclohexyl.

Those compounds of formula I are particularly preferred wherein R$_3$ is C$_1$-C$_{18}$alkyl, (CH$_2$)$_m$COOR$_4$, benzyl or phenyl, preferably C$_1$-C$_{18}$alkyl or —(CH$_2$)$_m$COOR$_4$.

Interesting compounds of formula I are those wherein R$_1$ and R$_2$ are each independently of the other C$_1$-C$_4$alkyl, n is an integer from 4 to 6, $R_3$ is $C_1$–$C_{12}$alkyl or a radical —$(CH_2)_m$—$COOR_4$,
$R_4$ is $C_1$–$C_{12}$alkyl,
m is 1,
X is O, S or $NR_6$, and
$R_3$ and $R_6$ together with the linking N atom are a radical

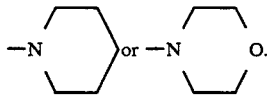

The reaction of cyanuric chloride with different protic reactants is known per se and described, inter alia, in "Comprehensive Heterocyclic Chemistry", Volume 3, Part 2B, page 482 (Pergamon Press, 1884) or by W. F. Beech in J. Chem. Soc. (C), 1967, pp. 466–472. Further particulars will be found in the publication "s-Triazines and Derivatives" by Edwin M. Smolin and Lorence Rapoport in "The Chemistry of Heterocyclic Compounds", (Interscience New York, London, 1959), 13, page 48, and U.S. Pat. No. 4,161,592.

The compounds of formula I may thus be prepared by reacting cyanuric chloride (II) with ω-(hydroxyphenyl)alkanols (III) (reaction A) and alcohols, mercaptans or amines (reaction B) in accordance with the following scheme:

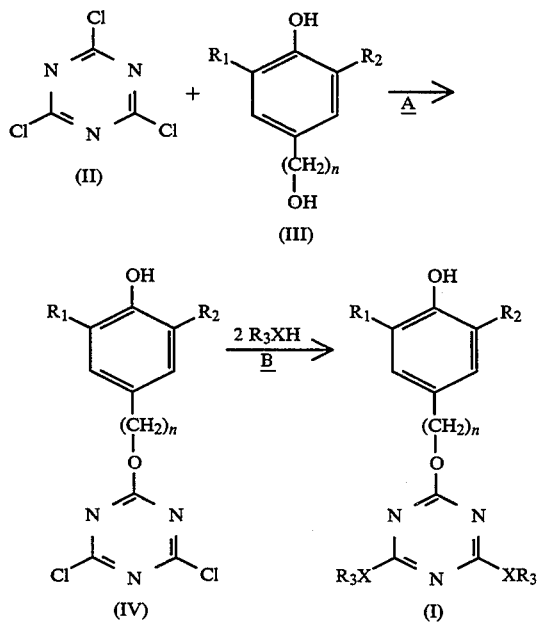

wherein $R_1$, $R_2$, $R_3$, X and n are as defined above in connection with formula I.

Reaction step A:

1 equivalent of cyanuric chloride (II) is conveniently reacted with 1 to 1.3 equivalents of the corresponding phenolic alcohol (III) in the presence of a weak base in an organic solvent. Suitable bases may typically be nitrogenous bases such as pyridine, trimethylpyridine, triethylamine or piperdine, preferably pyridine and trimethylpyridine. Also suitable are inorganic bases such as alkali metal carbonates or hydroxides. It is expedient to use 1 equivalent of the appropriate base.

The reaction may be carried out in an aprotic solvent such as acetone, acetone/water, tetrahydrofuran or diethyl ether. The reaction temperature may be in range between the melting point and the boiling point of the reaction mixture. The reaction may conveniently be carried out in the temperature range from 0° C. to 80° C., preferably from 5° C. to 50° C.

The resultant product can likewise be purified by known standard methods, typically by washing, extraction with an organic solvent, distillation, crystallisation and/or chromatography.

The condensation of the alcohols with cyanuric chloride may also be carried in a high-boiling solvent, as in toluene or xylene, in the temperature range from c. 100° C. to c. 150° C. In this process the hydrogen chloride that forms is conveniently expelled with a stream of dry nitrogen. This process is described in Erdöl, Kohle, Erdgas-Petrochem. 25, 3 (1972), pp. 130–135.

Reaction step B:

The reaction of the compounds (IV) with alcohols, mercaptans or amines is conveniently carried out in the presence of a base in the temperature range from 5° C. to 100° C. It is expedient to use at least 2 molar equivalents, but also more, typically 2.4 molar equivalents, of the respective amine, alcohol or mercaptan. In the reaction of the compounds (IV) with amines it is also possible to carry out the reaction with at least 4 molar equivalents of the amine.

Bases which may suitably be used are typically bases such as trimethylpyridine, tertiary amines such as triethylamine, or sodium and lithium alcoholates, typically sodium ethanolate or lithium methanolate. A slight excess of base is conveniently used, e.g. 2 to 2.4 molar equivalents.

When reacting compounds (IV) with alcohols or phenols, the corresponding sodium or lithium alcoholates or phenolates may first be formed.

It is usually expedient to isolate the intermediate (IV) after reaction step A and to use it in purified form for the following reaction step B. However, it is also possible to carry out the reaction as a single-step reaction without isolation of the intermediate (IV).

Cyanuric chloride is known per se and commercially available.

The ω-(hydroxyphenyl)alkanols of formula III can be prepared by known methods or by methods analogous to known ones. Thus the compounds of formula III may be obtain by the process disclosed in U.S. Pat. No. 4,260,832 or by a process analogous thereto. In this process the 2,6-disubstituted phenols are reacted in the presence of an alkali metal, alkali metal hydroxide or alkoxide in the temperature range from 200° C. to 300° C., while removing the water of reaction with the corresponding α,ω-alkanediols [HO—$(CH_2)_n$—OH]. The product can afterwards be isolated by conventional methods and used for the reaction with cyanuric chloride. It is, however, also possible to use the crude product direct for the preparation of compounds of formula I without further purification.

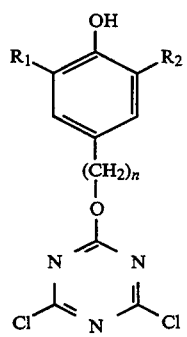

wherein
R₁ and R₂ are each independently of the other hydrogen, $C_1$–$C_{24}$alkyl, phenyl-substituted $C_1$–$C_4$alkyl, unsubstituted or $C_1$–$C_4$alkyl-substituted $C_5$–$C_8$cycloalkyl, unsubstituted or $C_1$–$C_4$alkyl-substituted phenyl, with the proviso that both substituents R₁ and R₂ are not simultaneously hydrogen, and
n is an integer from 3 to 8,
are novel and therefore also an object of the invention. As already mentioned, they are educts for the preparation of the novel phenolic s-triazines.

The compounds of formula IV are prepared by reacting cyanuric chloride (II) with ω-(hydroxyphenyl)alkanols (II) by the above described method (reaction step A).

As already mentioned above, the compounds of formula I are suitable for stabilising organic materials susceptible to thermal, oxidative and/or light-induced degradation.

The use of the compounds of formula I for stabilising organic material susceptible to thermal, oxidative and/or light-induced degradation, as well as a process for stabilising organic material susceptible to thermal, oxidative and/or light-induced degradation, therefore comprises adding t said material at least one compound of formula I as claimed in claim 1.

The invention also relates to a composition comprising (a) an organic material susceptible to thermal, oxidative and/or light-induced degradation and (b) at least one compound of formula I.

Illustrative examples of such organic materials (a) are:

1. Polymers of monoolefins and diolefins, for example polypropylene, ployisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE). lo density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following methods:
a) radical polymerisation (normally under high pressure and at elevated temperature).
b) catalytic polymerisation using a catalyst that normally contains one or more than one metal of groups IVb, Vb, VIb, VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalyst can be used by themselves in the polymerisation or further activators may be used, typically meal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile; and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The particularly preferred component (a) is a synthetic organic polymer, a mixture of such polymers or a lubricant.

In preferred compositions component (a) is an elastomer.

Component (a) may also be in particular a polyolefin or a styrene-containing polymer.

The use of compounds of formula I as antioxidants in synthetic organic polymers is to be highlighted.

The suitable lubricants and hydraulic fluids may be based on mineral or synthetic oils or mixtures thereof. The lubricants are known to the skilled person and described in the pertinent technical literature, for example in Dieter Klamann, "Schmierstoffe und verwandte Produkte" (Lubricants and Related Products), Verlag Chemie, Weinheim, 1982, in Schewe-Kobek, "Das Schmiermittel-Taschenbuch" (The Lubricant Handbook), Dr. Alfred Hüthig-Verlag, Heidelberg, 1974) and in "Ullmanns Enzyklopädie der technischen Chemie", (Encyclopedia of Industrial Chemistry), Vol. 13, pages 85–94 (Verlag Chemie, Weinheim, 1977).

The novel compositions conveniently comprise 0.01 to 10%, preferably 0.05 to 5%, most preferably 0.1 to 2%, of at least one compound of formula I, based on the total weight of the material to be stabilised.

In addition to the compounds of formula I, the novel compositions may additionally comprise conventional additives, typically:

1. Antioxidants 1.1. Alkylated monophenols, for example 2,6-di-tert-butyl-4-methylphenol,2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl4-hydroxyanisole, 3,5-di-tert-butyl-4-hydroxyanisole, 3,5-di-tert-butyl-4-hydroxyphenylstearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl)-pentane.

1.6. O-, N- and S-benzyl compounds, for example 3,5,3',5'-tetra-tert-butyl-4,4'-dihydroxy-debenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)propionic acid with mono- or poly-hydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3- thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert.-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)benztriazole, 2-(3',5'-di-tert-butyl-2'-hydroxyphenyl)benztriazole, 2-(5'-tert-butyl-2'-hydroxyphenyl)-benztriazole, 2-(2'-hydroxy-5'-(1,1,3,3,-tetramethylbutyl)phenyl)-benztriazole, 2-(3',5'-di-tert-butyl-2'-hydroxyphenyl)-5-chlor-benztriazole, 2-(3'-tert-butyl-2'-hydroxy-5'-methylphenyl)-5-chlor-benztriazole, 2-(3'-sec-butyl-5'-tert-butyl-2'-hydroxyphenyl)-benztriazole, 2-(2'-hydroxy-4'-octoxyphenyl)-benztriazole, 2-(3',5'-di-tert-amyl-2'-hydroxyphenyl)-benztriazole, 2-(3',5'-bis-(α,α-dimethylbenzyl)-2'-hydroxyphenyl)-benztriazole, mixture of 2-(3'-tert-butyl-2'-hydroxy-5'-(2-octyloxycarbonylethyl)phenyl)-5-chlor-benztriazole, 2-(3'-tert-butyl-5'-[2-(2-ethylhexyloxy)-carbonylethyl]-2'-hydroxyphenyl)-5-chlor-benztriazole, 2-(3'-tert-butyl-2'-hydroxy-5'-(2-methoxycarbonylethyl)phenyl)-5-chlor-benztriazole, 2-(3'-tert-butyl-2'-hydroxy-5'-(2-methoxycarbonylethyl)phenyl)-benztriazole, 2-(3'-tert-butyl-2'-hydroxy-5'-(2-octyloxycarbonylethyl)phenyl)-benztriazole, 2-(3'-dodecyl-2'-hydroxy-5'-methylphenyl)-benztriaazole, und 2-(3'-tert-butyl-2'-hydroxy-5'-(2-isooctyloxycarbonylethyl)phenyl -benztriazole, 2,2'-methylene-bis[4-(1,1,3,3,-tetramethylbutyl)-6-benztriazole-2-yl-phenol]; the transesterification product of 2-[3'-tert-butyl-5'-(2-methoxycarbonylethyl)-2'-hydroxyphenyl]-2H -benztriazole with polyethylene gylcol 300; [R-$CH_2CH_2$-COO ($CH_2$)$_3$]$_2$, where R = 3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl)resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-di-phenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazasprio[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'- ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(-salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetaladipoyl dihydrazide, N,N'-bis(salicyloyl)oxalyl dihydrazide, N,N'-bis(salicyloyl)-thiopropionyl dihydrazide.

4. Further phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,6-di-tert-butyl-4-methylphenyl)-pentaeryt hritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, fluorescent whitening agents, flameproofing agents, antistatic agents and blowing agents.

11. Benzofuranones and indolinones, for example those disclosed in U.S. Pat. No. 4,325,863 or U.S. Pat. No. 4,338,244.

In addition to the above additives, lubricant formulations may contain other additives, typically aminic antioxidants, metal deactivators, rust inhibitors, viscosity index improvers, pour-point depressants, dispersants and antiwear additives.

The invention is illustrated in more detail by the following Examples in which, as also throughout the remainder of the description and in the claims, parts and percentages are by weight, unless otherwise indicated.

1) Preparation of the dichloro intermediates

EXAMPLE 1

2-[6'-(3''-tert-butyl-5''-methyl-4''-hydroxyphenyl)hexyloxy]-4,6-dichloro-1,3,5-triazine A solution of 76.7 g (290 mmol; 1.3 equivalents) of 6-(3'-tert-butyl-5'-methyl-4'-hydroxyphenyl)hexanol in 10 ml of acetone is added to a suspension of 40.57 g (220 mmol) of cyanuric chloride in 300 ml of acetone and then 29.3 ml (220 mmol) of 2,4,6-collidine are added dropwise over 45 minuten at 5° C. The reaction mixture is stirred for 5 hours at room temperature and then poured on to c. 250 ml of ice/water and extracted with ethyl acetate. The organic phases are concentrated by evaporation and the crude product is purified over a short column of silica gel (600 g; hexane/ethyl acetate 40:1→19:1), giving 50.0 g (55% of theory) of the desired phenolic dichlorotriazine as a white powder with a melting point of 63°–65° C. (hexane).

The analytical data are shown in Table 1.

EXAMPLE 2

The dichlorotriazine of Example 2 is prepared using 4-(3',5'-di-tert-butyl-4'-hydroxyphenyl)butanol by the method described in Example 1. Structures and analytical data of this compound are shown in Table 1.

TABLE 1

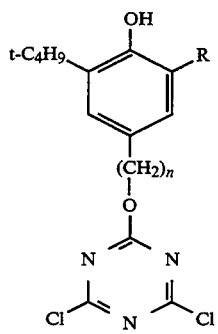

| Example | R | n | Melting point [°C.] | Elemental analysis [%] | | | | | | | |
|---|---|---|---|---|---|---|---|---|---|---|---|
| | | | | C calcd | C found | H calcd | H found | N calcd | N found | Cl calcd | Cl found |
| 1 | $CH_3$ | 6 | 63–65 | 58.25 | 58.38 | 6.60 | 6.61 | 10.19 | 10.16 | 17.20 | 16.81 |
| 2 | $t-C_4H_9$ | 4 | 72–74 | 59.16 | 59.18 | 6.68 | 6.94 | 9.86 | 9.84 | 16.63 | 16.69 |

B) Preparation of the novel s-triazines

EXAMPLE 3

2-[6'-(3''-tert-butyl-5''-methyl-4''-hydroxyphenyl)hexyloxy-4,6-bis-octylthio-1,3,5-triazine 11.5 ml (63 mmol) of a 5.4N solution of sodium methylate in methanol are added dropwise to a solution of 12.4 g (30 mmol) of the compound of Example 1 and 10.9 ml (63 mmol) of 1-octanethiol in 120 ml of toluene at 5° C. under nitrogen. The suspension is then warmed to room temperature, stirred for 1 hour, then filtered and the filtrate is poured into an aqueous saturated solution of ammonium chloride. The product is then extracted with ethyl acetate. The organic phase is dried and concentrated and the resultant crude product is purified by chromatography (SiO₂; hexane/ethyl acetate 40:1). Yield: 11.3 g (60% of theory) of the title product as a colourless oil. The analytical data are shown in Table 2.

EXAMPLES 4–7

The compounds of Examples 4–7 are prepared using appropriate dichlorotriazine compounds and mercaptans by the method described in Example 3. Structures and analytical data of this compound are shown in Table 2.

EXAMPLE 8

2-[4'-(3'',5''-Di-tert-butyl-4''-hydroxyphenyl)butoxy]-4,6-bis(piperidin-1-yl)-1,3,5-triazine 13.04 ml (132 mmol) of piperidine are added dropwise at 5° C. to a solution of 12.79 g (30 mmol) of the compound of Example 2 in 120 ml of tetrahydrofuran. The reaction mixture is stirred for 2 hours at room temperature and then filtered over ®Hyflo. The filtrate is poured into an aqueous saturated solution of ammonium chloride and extracted with ethyl acetate. The organic phase is dried and concentrated and the crude product is purified by recrystallisation from acetonitrile, giving 14.2 g (90% of theory) of a white powder with a melting point of 118°–119° C. Further analytical data are shown in Table 2.

EXAMPLES 9–11

The compounds of Examples 9–11 are prepared using appropriate dichlorotriazines and secondary amines by the method described in Example 8. The structures and analytical data are shown in Table 2.

EXAMPLE 12

2-[6'-(3''-tert-Butyl-5''-methyl-4''-hydroxyphenyl)hexyloxy-4,6-dimethoxy-1,3,5-triazine 10.9 ml (59 mmol) of a 5.4N solution of sodium methylate in methanol are added dropwise at 5° C. to a solution of 11.5 g (28 mmol) of the compound of Example 1 in 100 ml of toluene. The reaction mixture is stirred for 2 hours at room temperature, then poured into an aqueous saturated solution of ammonium chloride and afterwards extracted with ethyl acetate. The organic phase is dried and concentrated, and the crude product is purified by chromatography (SiO₂; hexane/ethyl acetate 19:1→9:1), giving 9.13 g (81% of theory) of the title product as white powder with a melting point of 62° C. Further data are shown in Table 2.

EXAMPLES 13–17

The compounds of Examples 13–17 are prepared using an appropriate solution of sodium or lithium alcoholate or phenolate by the method described in Example 12. The structures and analytical data are shown in Table 2.

TABLE 2

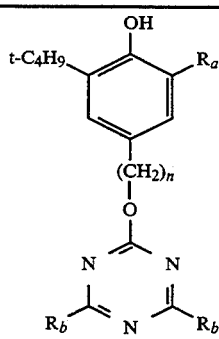

| Cmpd of Ex. | n | $R_a$ | $R_b$ | m.p. | C calcd | C found | H calcd | H found | N calcd | N found | S calcd | S found |
|---|---|---|---|---|---|---|---|---|---|---|---|---|
| 3 | 6 | CH$_3$ | S—$^n$C$_8$H$_{17}$ | oil | 68.41 | 68.27 | 9.73 | 9.89 | 6.65 | 6.54 | 10.15 | 10.12 |
| 4 | 6 | CH$_3$ | SCH$_2$COO$^i$C$_8$H$_{17}$* | oil | 64.22 | 64.36 | 8.76 | 8.80 | 5.62 | 5.56 | 8.57 | 8.09 |
| 5 | 4 | t-C$_4$H$_9$ | S—$^n$C$_8$H$_{17}$ | oil | 68.79 | 68.98 | 9.83 | 9.86 | 6.50 | 6.33 | 9.92 | 9.86 |
| 8 | 4 | t-C$_4$H$_9$ | —N(piperidinyl) | 118–119 | 71.09 | 71.09 | 9.43 | 9.53 | 13.37 | 13.12 | | |
| 9 | 6 | CH$_3$ | —N(morpholinyl) | 123–125 | 65.47 | 65.48 | 8.44 | 8.63 | 13.63 | 13.46 | | |
| 10 | 6 | CH$_3$ | —N(piperidinyl) | 117–118 | 70.69 | 70.62 | 9.29 | 9.54 | 13.74 | 13.62 | | |
| 12 | 6 | CH$_3$ | OCH$_3$ | 62 | 65.48 | 64.98 | 8.24 | 8.24 | 10.41 | 10.48 | | |
| 13 | 6 | CH$_3$ | OC$_4$H$_9$ | oil | 68.96 | 68.97 | 9.30 | 9.46 | 8.62 | 8.52 | | |
| 6 | 6 | CH$_3$ | —SC$_6$H$_5$ | — | 68.65 | 68.77 | 6.66 | 6.91 | 7.50 | 7.25 | 11.45 | 11.31 |
| 7 | 6 | CH$_3$ | —SCH$_2$—C$_6$H$_5$ | — | 69.47 | 69.36 | 7.03 | 7.14 | 7.15 | 7.27 | 10.91 | 11.17 |
| 11 | 6 | CH$_3$ | —N[CH$_2$CH(C$_2$H$_5$)C$_4$H$_9$]$_2$ | — | 75.95 | 75.98 | 11.64 | 11.66 | 8.52 | 8.50 | | |
| 14 | 6 | CH$_3$ | —O—cyclohexyl | — | 71.21 | 69.35 | 9.15 | 9.00 | 7.79 | 7.74 | | |
| 15 | 6 | CH$_3$ | —O—CH$_2$—C$_6$H$_5$ | — | 73.49 | 73.32 | 7.44 | 7.51 | 7.56 | 7.40 | | |
| 16 | 6 | CH$_3$ | —O—C(CH$_3$)$_2$CH$_2$NH–C(CH$_3$)$_2$– | 136–148 | 69.79 | 69.17 | 9.71 | 9.95 | 10.71 | 10.40 | | |
| 17 | 6 | CH$_3$ | —O—(3,5-di-t-C$_4$H$_9$-phenyl) | 50–60 | 76.66 | 75.85 | 9.25 | 9.31 | 5.59 | 5.49 | | |

*As educt ®IOMA supplied by Atochem was used
[HS—CH$_2$—CO—O—$^i$C$_8$H$_{17}$, wherein $^i$C$_8$H$_{17}$ is a mixture of octyl isomers]

EXAMPLE 18

Stabilisation of polypropylene

Polypropylene prestabilised with 0.3% of calcium stearate are blended with distearyl dithiopropionate (DSTDP) and 0.1% of stabiliser indicated in Table 3 and the blend is then kneaded in a Brabender plastograph at 200° C. for 10 minutes. The composition so obtained is subsequently moulded in a platen press having a surface temperature of 260° C. to 1 mm sheets from which strips 1 cm wide and 10 cm long are cut.

For comparison purposes, a further specimen without stabiliser is prepared. Several such strips cut from each sheet are hung in a circulating air oven at 135° C. and 149° C., and observed at regular intervals. The oxidative degradation of these strips is recognisable from an initially circular yellowing. A measure of the stability of the specimen is the time in days to the onset of decomposition. The results are reported in the following Table 3.

TABLE 3

| Stabilisers | Number of days of oven ageing until the onset of decomposition | |
|---|---|---|
| | at 135 °C. | at 149 °C. |
| without | 1 | <1 |
| DSTDP [0.3%] | 50 | 11 |
| DSTDP [0.3%] + compound 3 [0.1%] | 292 | 95 |
| DSTDP [0.3%] + compound 4 [0.1%] | 276 | 88 |
| DSTDP [0.3%] + compound 5 [0.1%] | 207 | 57 |
| DSTDP [0.3%] + compound 9 [0.1%] | 213 | 60 |
| DSTDP [0.3%] + compound 10 [0.1%] | 210 | 59 |

EXAMPLE 19

Stabilisation of acrylonitrile/butadiene/styrene terpolymer (ABS) Each of the stabilisers of Table 4 is dissolved in 40 ml of a mixture of hexane and isopropanol. With efficient stirring, the solution is added to a dispersion of 100 g of ABS in 600 ml of water, whereupon the solution is completely absorbed by the ABS within 1 minute. The polymer powder containing stabiliser is isolated by filtration and dried for 40 hours at 40° C. under vacuum.

The further processing steps are also carried out for comparison purposes with a sample that does not contain stabiliser.

To the dry powder are added, as pigment, 2% of titanium dioxide and, as lubricant, 1% of ethylene bis(stearamide). The mixture is then compounded for 4 minutes at 180° C. on a two-roll mill.

A 0.88 mm sheet is moulded from the rolled sheet at 175° C. and samples measuring 45×17 mm² are punched therefrom. The test for the effectiveness of the added stabilisers is carried out by heat ageing in a circulating air oven at 180° C. The criterion is the colour development after 45 minutes. The colour intensity is determined in accordance with ASTM D 1925-79 (Yellowness-Index). The test results are reported in Table 4. Higher values denote more intensive yellowing. The tests show that yellowing is diminished by the compounds of this invention.

TABLE 4

| Stabilisers | Yellowness Index after 45 minutes at 180 °C. |
|---|---|
| without | 60 |
| DLTDP [0.5%] | 75 |
| DLTDP [0.5%] + compound 3 [0.25%] | 31 |
| DLTDP [0.5%] + compound 4 [0.25%] | 33 |
| DLTDP [0.5%] + compound 9 [0.25%] | 30 |
| DLTDP [0.5%] + compound 12 [0.25%] | 30 |
| DLTDP [0.5%] + compound 13 [0.25%] | 32 |

DLTDP = dilaurylthiodipropionate

EXAMPLE 20

Stabilisation of polyisoprene 0.1% of each of the 5 stabilisers listed in Table 5 is incorporated into 200 g of ®IR Cariflex 305 (Shell) at 60° C. on a two-roll mill and the blend is then moulded to 10 mm sheets at 90° C. for 10 minutes. These sheets are aged at 70° C. in a circulating air oven. After 7 days ageing the Mooney viscosity (ML 1+4(100)) is determined according to ASTM D 1646. The less the original viscosity number changes after oven ageing, the better the stabilising effect of the compound employed. The original viscosity number is 60. The results are reported in Table 5.

TABLE 5

| Stabiliser | Mooney viscosity after 7 days oven ageing at 70 °C. |
|---|---|
| without | 24 |
| compound 4 | 51 |
| compound 5 | 50 |
| compound 8 | 49 |
| compound 11 | 48 |

EXAMPLE 21

Stabilisation of acrylonitrile/butadiene/styrene terpolymer (ABS)

The compounds listed in Table 6 are tested in accordance with the method described in Example 19.

TABLE 6

| Stabilisers | Yellowness Index after 45 minutes at 180 °C. |
|---|---|
| without | 66 |
| DLTDP [0.5%] + compound 6 [0.25%] | 40 |
| DLTDP [0.5%] + compound 7 [0.25%] | 41 |
| DLTDP [0.5%] + compound 11 [0.25%] | 39 |
| DLTDP [0.5%] + compound 14 [0.25%] | 36 |
| DLTDP [0.5%] + compound 15 [0.25%] | 42 |
| DLTDP [0.5%] + compound 16 [0.25%] | 44 |
| DLTDP [0.5%] + compound 17 [0.25%] | 39 |

DLTDP = dilaurylthiodipropionate

What is claimed is:

1. A compound of formula I

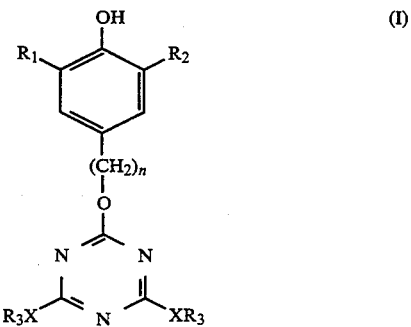

wherein

R₁ and R₂ are each independently of the other hydrogen, $C_1$-$C_{24}$alkyl, phenyl-substituted $C_1$-$C_4$alkyl, unsubstituted or $C_1$-$C_4$alkyl-substituted $C_5$-$C_8$cycloalkyl, unsubstituted or $C_1$-$C_4$alkyl-substituted phenyl, with the proviso that both substituents $R_1$ and $R_2$ are not simultaneously hydrogen, n is an integer from 3 to 8, $R_3$ is $C_1$-$C_{18}$alkyl which is interrupted by —O—, —S— or —NR₄—, unsubstituted or $C_1$-$C_4$alkyl-substituted $C_5$-$C_8$cycloalkyl, phenyl-substituted $C_1$-$C_4$alkyl, unsubstituted or $C_1$-$C_{12}$alkyl-substituted phenyl or a radical —(CH₂)ₘ—COOR₄

$R_4$ is $C_1$–$C_{18}$alkyl, unsubstituted or $C_1$–$C_4$alkyl-substituted $C_5$–$C_8$cycloalkyl, benzyl or phenyl, m is 1 or 2, X is O, S, or $NR_6$, and $R_6$ is hydrogen or $C_1$–$C_{12}$alkyl, or $R_3$ and $R_6$ together with the linking N-atom are a radical

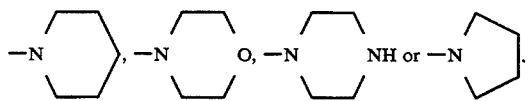

2. A compound according to claim 1, wherein X is S or $NR_6$.

3. A compound according to claim 1, wherein X is S.

4. A compound according to claim 1, wherein n is an integer from 4 to 6.

5. A compound according to claim 1, wherein $R_1$ and $R_2$ are each independently of the other $C_1$–$C_4$alkyl or cyclohexyl.

6. A compound according to claim 1, wherein $R_3$ is $C_1$–$C_{18}$alkyl, $(CH_2)_m COOR_4$, benzyl or phenyl.

7. A compound according to claim 1, wherein $R_3$ is $C_1$–$C_{18}$alkyl or —$(CH_2)_m COOR_4$.

8. A compound according to claim 1, wherein $R_1$ and $R_2$ are each independently of the other $C_1$–$C_4$alkyl, n is an integer from 4 to 6, $R_3$ is $C_1$–$C_{12}$alkyl or a radical —$(CH_2)_m$—$COOR_4$, $R_4$ is $C_1$–$C_{12}$alkyl, m is 1, X is O, S or $NR_6$, and $R_3$ and $R_6$ together with the linking N atom are a radical

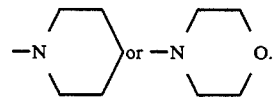

* * * * *